United States Patent
Papas

(10) Patent No.: US 12,029,636 B2
(45) Date of Patent: *Jul. 9, 2024

(54) STACKED TISSUE ENCAPSULATION DEVICE SYSTEMS WITH OR WITHOUT OXYGEN DELIVERY

(71) Applicant: Arizona Board of Regents on Behalf of the University of Arizona, Tucson, AZ (US)

(72) Inventor: Klearchos K. Papas, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 119 days.

This patent is subject to a terminal disclaimer.

(21) Appl. No.: 17/902,689

(22) Filed: Sep. 2, 2022

(65) Prior Publication Data

US 2023/0000612 A1    Jan. 5, 2023

Related U.S. Application Data

(63) Continuation of application No. 16/347,388, filed as application No. PCT/US2017/060034 on Nov. 3, 2017, now Pat. No. 11,446,133.

(60) Provisional application No. 62/417,017, filed on Nov. 3, 2016.

(51) Int. Cl.
| | |
|---|---|
| *A61L 31/00* | (2006.01) |
| *A61F 2/02* | (2006.01) |
| *A61L 27/22* | (2006.01) |
| *A61L 27/52* | (2006.01) |
| *A61L 27/54* | (2006.01) |

(52) U.S. Cl.
CPC ............ *A61F 2/022* (2013.01); *A61L 27/225* (2013.01); *A61L 27/227* (2013.01); *A61L 27/52* (2013.01); *A61L 27/54* (2013.01); *A61F 2220/0075* (2013.01)

(58) Field of Classification Search
None
See application file for complete search history.

(56) References Cited

U.S. PATENT DOCUMENTS

| | | |
|---|---|---|
| 4,902,476 A | 2/1990 | Gordon et al. |
| 5,169,390 A | 12/1992 | Athayde et al. |
| 5,324,518 A | 6/1994 | Orth et al. |
| 5,368,028 A | 11/1994 | Palti |
| 5,595,621 A | 1/1997 | Light et al. |
| 5,626,561 A | 5/1997 | Butler et al. |
| 5,713,888 A | 2/1998 | Brauker et al. |
| 5,741,330 A | 4/1998 | Brauker et al. |
| 5,814,405 A | 9/1998 | Branca et al. |
| 5,837,234 A | 11/1998 | Yapel et al. |
| 5,843,069 A | 12/1998 | Butler et al. |
| 5,882,354 A | 3/1999 | Brauker et al. |
| 5,980,889 A | 11/1999 | Butler et al. |
| 6,060,640 A | 5/2000 | Pauley et al. |
| 6,143,293 A | 11/2000 | Calvert et al. |
| 6,156,305 A | 12/2000 | Brauker et al. |
| 6,197,575 B1 | 3/2001 | Griffith et al. |
| 6,562,616 B1 | 5/2003 | Toner et al. |
| 7,659,219 B2 | 2/2010 | Biran et al. |
| 7,892,222 B2 | 2/2011 | Bloch et al. |
| 8,278,106 B2 | 10/2012 | Martinson et al. |
| 8,518,123 B2 | 8/2013 | Jensen et al. |
| 8,647,861 B2 | 2/2014 | Ingber et al. |
| 9,433,557 B2 | 9/2016 | Baetge et al. |
| 10,695,379 B2 | 6/2020 | Greenwood et al. |
| 11,033,666 B2 | 6/2021 | Ferrante et al. |
| 11,446,133 B2 | 9/2022 | Papas |
| 2003/0054544 A1 | 3/2003 | Gruenberg |
| 2003/0087427 A1 | 5/2003 | Colton et al. |
| 2003/0129736 A1 | 7/2003 | Mitrani |
| 2004/0010320 A1 | 1/2004 | Huckle et al. |

(Continued)

FOREIGN PATENT DOCUMENTS

| | | |
|---|---|---|
| CA | 3042709 | 8/2018 |
| CN | 101123984 | 2/2008 |

(Continued)

OTHER PUBLICATIONS

Krishnan et al., "Cellular Immunoisolation for Islet Transplantation by a Novel Dual Porosity Electrospun Membrane," Transplantation Proceedings, vol. 43, No. 9, Nov. 2011, pp. 3256-3261.

Lemons et al., "Biomaterials Science: An Introduction to Materials In Medicine," Elsevier Science, 2004, Table of Contents and Preface only.

Official Action for Australia Patent Application No. 2021204321, dated Jan. 19, 2023, 4 pages.

Notice of Allowance (with English translation) for China Patent Application No. 201780081318.9, dated Oct. 19, 2022, 6 pages.

(Continued)

*Primary Examiner* — Susan T Tran

(74) *Attorney, Agent, or Firm* — Sheridan Ross P.C.

(57) ABSTRACT

Systems featuring two or more encapsulation devices stacked together. The encapsulation devices house cells, such as but not limited to islet cells or stem cell derived beta cells or the like. e.g., for regulating blood glucose, or other cells or spheroids that can produce and release a therapeutic agent that is useful in the body, etc. The system may feature oxygen delivery, or in some cases no exogenous oxygen is delivered and vascularization of the device can help provide oxygen and other needed nutrient to the cells. The system of the present invention may be used in conjunction with other therapies such as an artificial pancreas. Stacking the devices with blood vessel formation around and in between them may allow for a decrease in the footprint that would be needed for implantation.

17 Claims, 3 Drawing Sheets

(56) References Cited

U.S. PATENT DOCUMENTS

| | | |
|---|---|---|
| 2004/0024342 A1 | 2/2004 | Weitzel et al. |
| 2004/0133188 A1 | 7/2004 | Vardi et al. |
| 2004/0166141 A1 | 8/2004 | Cerami et al. |
| 2004/0197374 A1 | 10/2004 | Ghabrial et al. |
| 2005/0136092 A1 | 6/2005 | Rotem et al. |
| 2005/0221485 A1 | 10/2005 | Bader |
| 2005/0267440 A1 | 12/2005 | Herman et al. |
| 2006/0013835 A1 | 1/2006 | Anderson et al. |
| 2006/0019333 A1 | 1/2006 | Leblanc et al. |
| 2007/0061015 A1 | 3/2007 | Biris et al. |
| 2007/0066138 A1 | 3/2007 | Ferrari et al. |
| 2008/0021436 A1 | 1/2008 | Wolpert et al. |
| 2009/0074832 A1 | 3/2009 | Zussman et al. |
| 2009/0110669 A1 | 4/2009 | Schneiderman et al. |
| 2010/0082114 A1 | 4/2010 | Gingras et al. |
| 2010/0124564 A1 | 5/2010 | Martinson et al. |
| 2010/0130916 A1 | 5/2010 | Barkai et al. |
| 2010/0160760 A1 | 6/2010 | Shults et al. |
| 2010/0172952 A1 | 7/2010 | Srouji et al. |
| 2010/0196439 A1 | 8/2010 | Beck et al. |
| 2010/0228110 A1 | 9/2010 | Tsoukalis |
| 2010/0240117 A1 | 9/2010 | Ying et al. |
| 2010/0255059 A1 | 10/2010 | Marquez et al. |
| 2011/0054589 A1 | 3/2011 | Bashiri et al. |
| 2011/0092949 A1 | 4/2011 | Wang |
| 2012/0041355 A1 | 2/2012 | Edman et al. |
| 2012/0245705 A1 | 9/2012 | Hasilo et al. |
| 2013/0289540 A1 | 10/2013 | Zeltser et al. |
| 2013/0344131 A1 | 12/2013 | Lo et al. |
| 2014/0014226 A1 | 1/2014 | Baetge et al. |
| 2014/0039383 A1 | 2/2014 | Dobbles et al. |
| 2014/0051162 A1 | 2/2014 | Nankervis |
| 2014/0052095 A1 | 2/2014 | Dobbles et al. |
| 2014/0088347 A1 | 3/2014 | Frigstad et al. |
| 2014/0257515 A1* | 9/2014 | So ............... A61M 31/002 623/23.64 |
| 2014/0308315 A1 | 10/2014 | Knezevich et al. |
| 2015/0112247 A1 | 4/2015 | Papas et al. |
| 2015/0129497 A1 | 5/2015 | Humes et al. |
| 2015/0273200 A1 | 10/2015 | Rotem et al. |
| 2015/0320836 A1 | 11/2015 | Itkin-Ansari et al. |
| 2015/0359472 A1 | 12/2015 | Botvinnick et al. |
| 2016/0022180 A1 | 1/2016 | Joseph et al. |
| 2016/0038207 A1 | 2/2016 | Wei et al. |
| 2016/0082236 A1 | 3/2016 | Botvinick et al. |
| 2016/0123848 A1 | 5/2016 | Griffin et al. |
| 2016/0184569 A1 | 6/2016 | Bouche et al. |
| 2017/0072074 A1 | 3/2017 | Gladnikoff et al. |
| 2017/0173262 A1 | 6/2017 | Veltz |
| 2018/0000395 A1 | 1/2018 | Lucisano et al. |
| 2018/0126134 A1 | 5/2018 | Cully et al. |
| 2018/0263238 A1 | 9/2018 | Flanagan et al. |
| 2018/0298343 A1 | 10/2018 | Sivakumaran |
| 2018/0318566 A1 | 11/2018 | Ferrante et al. |
| 2018/0344665 A1 | 12/2018 | Isenburg et al. |
| 2019/0076840 A1 | 3/2019 | Gottardi et al. |
| 2019/0136176 A1 | 5/2019 | Kawachi et al. |
| 2019/0211294 A1 | 7/2019 | Karnieli |
| 2019/0224377 A1 | 7/2019 | Papas |
| 2019/0328289 A1 | 10/2019 | Papas |
| 2019/0336267 A1 | 11/2019 | Tempelman et al. |
| 2020/0054257 A1 | 2/2020 | Papas |
| 2020/0063085 A1 | 2/2020 | Papas |
| 2021/0386333 A1 | 12/2021 | Papas |
| 2021/0401564 A1 | 12/2021 | Neuenfeldt et al. |
| 2022/0134074 A1 | 5/2022 | Papas |

FOREIGN PATENT DOCUMENTS

| | | |
|---|---|---|
| CN | 201337642 | 11/2009 |
| CN | 102012390 | 4/2011 |
| CN | 203915611 | 11/2014 |
| CN | 105163688 | 12/2015 |
| CN | 105792775 | 7/2016 |
| DE | 8909058 | 9/1989 |
| EP | 0344314 | 12/1989 |
| EP | 1351623 | 10/2003 |
| EP | 2508212 | 10/2012 |
| JP | H06-205665 | 7/1994 |
| JP | 2004-530431 | 10/2004 |
| JP | 2014-514942 | 6/2014 |
| KR | 20100035706 A * | 4/2010 |
| KR | 10-2012-0091008 | 8/2012 |
| KR | 10-2014-0023252 | 2/2014 |
| KR | 10-2016-0094391 | 8/2016 |
| WO | WO 91/00119 | 1/1991 |
| WO | WO 01/12158 | 2/2001 |
| WO | WO 02/100335 | 12/2002 |
| WO | WO 2006/106506 | 10/2006 |
| WO | WO 2008/100559 | 8/2008 |
| WO | WO 2010/061387 | 6/2010 |
| WO | WO 2012/136701 | 10/2012 |
| WO | WO 2014/173441 | 10/2014 |
| WO | WO 2015/145264 | 10/2015 |
| WO | WO 2018/067813 | 4/2018 |
| WO | WO 2018/085714 | 5/2018 |
| WO | WO 2018/089397 | 5/2018 |
| WO | WO 2018/102077 | 6/2018 |
| WO | WO 2018/144098 | 8/2018 |
| WO | WO 2018/144099 | 8/2018 |
| WO | WO 2022/094380 | 5/2022 |

OTHER PUBLICATIONS

Communication Pursuant to Article 94(3) for Europe Patent Application No. 17866485.0, dated Dec. 28, 2022, 6 pages.
Official Action for Korea Patent Application No. 2019-7015936, dated Nov. 29, 2022, 3 pages.
Official Action for Australia Patent Application No. 2021206840, dated Jan. 17, 2023, 3 pages.
Communication Pursuant to Article 94(3) for Europe Patent Application No. 17895433.5, dated Jan. 2, 2023, 4 pages.
Official Action for Australia Patent Application No. 2021202373, dated Oct. 24, 2022, 7 pages.
Official Action for Australia Patent Application No. 2019346547, dated Jan. 13, 2023, 6 pages.
Official Action (with English summary) for Japan Patent Application No. 2021-540389, dated Jan. 17, 2023, 6 pages.
Official Action for U.S. Appl. No. 16/647,338, dated Dec. 15, 2022, 9 pages.
Official Action for U.S. Appl. No. 16/347,147, dated Jan. 10, 2023, 15 pages.
Official Action for U.S. Appl. No. 16/347,160, dated Dec. 19, 2022, 19 pages.
Official Action for U.S. Appl. No. 17/387,595, dated Dec. 19, 2022, 20 pages.
Lemons et al., "Biomaterials Science: An Introduction to Materials In Medicine," Elsevier Science, 2004, pp. 88-89, 629, & 642 [best available quality].
Intent to Grant (with English translation) for China Patent Application No. 201780081104.1, dated Oct. 19, 2022, 6 pages.
Communication Pursuant to Article 94(3) for Europe Patent Application No. 17894862.6, dated Feb. 1, 2023, 9 pages.
Communication pursuant to Article 94(3) for Europe Patent Application No. 17875181.4, dated Feb. 9, 2023, 6 pages.
Official Action (no English translation available) for Korea Patent Application No. 10-2022-7028922, dated Feb. 3, 2023, 5 pages.
Official Action for Singapore Patent Application No. 11201905391W, dated Apr. 28, 2023, 4 pages.
Official Action for Australia Patent Application No. 2021206840, dated May 1, 2023, 4 pages.
Official Action for Australia Patent Application No. 2021206840, dated May 30, 2023, 3 pages.
Notice of Allowance for Australia Patent Application No. 202106840, dated Jun. 8, 2023, 4 pages.
Official Action for Korea Patent Application No. 10-2022-7037085, dated Jun. 20, 2023, 9 pages.

(56) References Cited

OTHER PUBLICATIONS

Official Action for Korea Patent Application No. 10-2022-7037086, dated Jun. 15, 2023, 6 pages.
Official Action (with English summary) for China Patent Application No. 201780081105.6, dated Apr. 18, 2023, 8 pages.
Official Action for Singapore Patent Application No. 11201905390Q, dated Apr. 28, 2023, 3 pages.
Notice of Allowance for Canada Patent Application No. 3114197, dated Apr. 17, 2023, 1 page.
Official Action (with English translation) for Korea Patent Application No. 10-2021-7012313, dated Mar. 3, 2023, 17 pages.
Official Action for Taiwan Patent Application No. 108134435, dated Jul. 18, 2023, 11 pages.
International Preliminary Report on Patentability for International (PCT) Application No. PCT/US2021/057526, dated May 11, 2023, 9 pages.
Notice of Allowance for U.S. Appl. No. 16/647,338, dated Mar. 24, 2023, 7 pages.
Notice of Allowance for U.S. Appl. No. 16/347,147, dated Apr. 17, 2023, 7 pages.
Corrected Notice of Allowance for U.S. Appl. No. 16/347,147, dated Apr. 20, 2023, 2 pages.
Official Action for U.S. Appl. No. 17/387,595, dated Apr. 10, 2023, 29 pages.
Official Action for U.S. Appl. No. 17/876,302, dated Apr. 3, 2023, 19 pages.
Official Action for U.S. Appl. No. 17/516,179, dated Jul. 11, 2023, 8 pages. Restriction Requirement.
U.S. Appl. No. 17/876,302, filed Jul. 28, 2022, Neuenfeldt et al.
"Membrane Basics," PermSelect—Silicone Gas Exchange Membranes, 2021, retrieved from https://www.permselect.com/membranes, 9 pages.
Carlsson et al., "Transplantation of macroencapsulated human islets within the bioartificial pancreas BAir to patients with type 1 diabetes mellitus," American Journal of Transplantation, vol. 18, 2018, pp. 1735-1744.
Geller et al., "Use of an Immunoisolation Device for Cell Transplantation and Tumor Immunotherapy," Annals New York Academy of Science, Date Unnknown, 14 pages.
Gholipourmalekabadi et al., "Oxygen-Generatin Biomaterials: A New, Viable Paradigm for Tissue Engineering?" Trends in Biotechnology, vol. 34, No. 12, Dec. 2016, pp. 1010-1021.
Knoepiler, "ViaCyte CEO Paul Laikind Interview: Trial Update, Melton's Concerns, & Future," The Niche, Mar. 2, 2015, retrieved from https://ipscell.com/2015/03/viacyte, 6 pages.
Krishnan et al., "Islet And Stem Cell Encapsulation For Clinical Transplantation," Review of Diabetic Studies, vol. 11, No. 1, 2014, pp. 84-101.
Lathuiliere et al., "Encapsulated Cellular Implants for Recombinant Protein Delivery and Therapeutic Modulation of the Immune System," International Journal of Molecular Sciences, vol. 16, 2015, pp. 10578-10600.
Lee et al., "Cytokines in Cancer Immunotherapy," Cancers, vol. 3, 2011, pp. 3856-3893.
Makadia et al., "Poly Lactic-co-Glycolic Acid (PLGA) as Biodegradable Controlled Drug Delivery Carrier," Polymers (Basel), vol. 3, No. 3, Sep. 1, 2011, pp. 1377-1397.
Manickavasagam et al., "Critical Assessment of Implantable Drug Delivery Devices in Glaucoma Management," Jounral of Drug Delivery, vol. 2013, No. 895013, Jul. 2013, 12 pages.
Suszynski et al., "Assessment of Tissue-Engineered Islet Graft Viability by Fluorine Magnetic Resonance Spectroscopy," Transplant Proc., vol. 43, No. 9, Nov. 2011, pp. 3221-3225.
Wang et al., "Overcoming foreign-body reaction through nanotopography: Biocompatibility and Immunoisolation properties of a nanofibrous membrane," Biomaterials, vol. 102, Sep. 30, 2016, pp. 249-258.
International Search Report and Written Opinion for International (PCT) Patent Application No. PCT/US2017/060036, dated Feb. 16, 2018, 14 pages.
Official Action for Australia Patent Application No. 2017355528, dated Aug. 20, 2020, 5 pages.
Official Action for Australia Patent Application No. 2017355528, dated Nov. 16, 2020, 4 pages.
Notice of Acceptance for Australia Patent Application No. 2017355528, dated Mar. 22, 2021, 4 pages.
Official Action for Australia Patent Application No. 2021204321, dated Jun. 6, 2022, 3 pages.
Official Action for China Patent Application No. 201780081318.9, dated Feb. 1, 2021, 8 pages.
Official Action for China Patent Application No. 201780081318.9, dated Sep. 1, 2021, 12 pages.
Official Action for China Patent Application No. 201780081318.9, dated Apr. 7, 2022, 22 pages.
Extended European Search Report for Europe Patent Application No. 17866485.0, dated Apr. 25, 2020, 9 pages.
Official Action for Korea Patent Application No. 10-2019-7015936, dated Feb. 22, 2022, 11 pages.
Official Action for Korea Patent Application No. 10-2019-7015936, dated Jul. 25, 2022, 5 pages.
International Search Report and Written Opinion for International (PCT) Patent Application No. PCT/US2017/060034, dated Jul. 12, 2018, 9 pages.
Official Action for Australia Patent Application No. 2017396753, dated Jul. 23, 2020, 4 pages.
Official Action for Australia Patent Application No. 2017396753, dated Jan. 27, 2021, 5 pages.
Notice of Acceptance for Australia Patent Application No. 2017396753, dated Apr. 20, 2021, 4 pages.
Official Action for Australia Patent Application No. 202106840, dated Jun. 6, 2022, 3 pages.
Official Action for China Patent Application No. 201780081104.1, dated Apr. 2, 2021, 10 pages.
Official Action for China Patent Application No. 201780081104.1, dated Dec. 2, 2021, 11 pages.
Official Action for China Patent Application No. 201780081104.1, dated Jun. 30, 2022, 27 pages.
Extended European Search Report for European Patent Application No. 17895433.5, dated Apr. 17, 2020, 7 pages.
Official Action for Korea Patent Application No. 10-2019-7015935, dated Feb. 8, 2022, 9 pages.
Notice of Allowance for Korea Patent Application No. 10-2019-7015935, dated Jul. 25, 2022, 3 pages.
International Search Report and Written Opinion for International (PCT) Patent Application No. PCT/US2017/060014, dated Jul. 10, 2018, 14 pages.
Official Action for Australian Patent Application No. 2017396754, dated Nov. 12, 2020, 7 pages.
Notice of Allowance for Australian Patent Application No. 2017396754, dated Jul. 21, 2021, 4 pages.
Official Action for China Patent Application No. 201780081103.7, dated Jan. 11, 2021, 11 pages.
Official Action for China Patent Application No. 201780081103.7, dated Nov. 1, 2021, 11 pages.
Notice of Allowance for China Patent Application No. 201780081103.7, dated Mar. 23, 2022, 2 pages.
Extended European Search Report for Europe Patent Application No. 17894862.6, dated May 20, 2020, 4 pages.
Official Action for Korea Patent Application No. 10-2019-7015937, dated Jan. 12, 2022, 14 pages.
Notice of Allowance for Korea Patent Application No. 10-2019-7015937, dated May 20, 2022, 6 pages.
Notice of Allowance for Korea Patent Application No. 10-2019-7015937, dated Jul. 22, 2022, 3 pages.
International Search Report and Written Opinion for International (PCT) Patent Application No. PCT/US2017/060043, dated Jun. 14, 2018, 9 pages.
Official Action for Australi Patent Application No. 2017366791, dated Jun. 22, 2020, 4 pages.
Notice of Allowance for Australia Patent Application No. 2017366791, dated Jan. 8, 2021, 4 pages.
Official Action for China Patent Application No. 201780081105.6, dated Aug. 9, 2021, 12 pages.

(56) References Cited

OTHER PUBLICATIONS

Official Action for China Patent Application No. 201780081105.6, dated Mar. 24, 2022, 12 pages.
Official Action for China Patent Application No. 201780081105.6, dated Sep. 29, 2022, 8 pages.
Extended European Search Report for Europe Patent Application No. 17875181.4, dated Apr. 28, 2020, 4 pages.
Official Action for Korea Patent Application No. 10-2019-7015938, dated Sep. 30, 2021, 5 pages.
International Search Report and Written Opinion for International (PCT) Patent Application No. PCT/US2019/052728, dated Dec. 13, 2019, 10 pages.
International Preliminary Report on Patentability for International (PCT) Application No. PCT/US2019/052728, dated Apr. 1, 2021, 9 pages.
Official Action for Australia Patent Application No. 2019346547, dated Feb. 9, 2022, 4 pages.
Official Action for Australia Patent Application No. 2019346547, dated Sep. 2, 2022, 4 pages.
Official Action for Canada patent Application No. 3114197, dated Jun. 6, 2022, 6 pages.
Partial Supplementary European Search Report for Europe Patent Application No. 19867716.3, dated May 23, 2022, 13 pages.
Extended European Search Report for Europe Patent Application No. 19867716.3, dated Oct. 6, 2022, 12 pages.
Official Action for India Patent Application No. 202117012735, dated Feb. 11, 2022, 5 pages.
Official Action (with English summary) for Japan Patent Application No. 2021-540389, dated Jun. 21, 2022, 7 pages.
Invitation to Pay additional Fees for International (PCT) Patent Application No. PCT/US2021/057526, dated Jan. 5, 2022, 3 pages.
International Search Report and Written Opinion for International (PCT) Patent Application No. PCT/US2021/057526, dated Mar. 2, 2022, 16 pages.
Official Action for U.S. Appl. No. 16/647,338, dated Jun. 16, 2022, 10 pages.
Official Action for U.S. Appl. No. 16/347,388, dated May 11, 2021, 10 pages.
Official Action for U.S. Appl. No. 16/347,388, dated Oct. 4, 2021, 10 pages.
Notice of Allowance for U.S. Appl. No. 16/347,388, dated May 12, 2022, 10 pages.
Corrected Notice of Allowance for U.S. Appl. No. 16/347,388, dated May 20, 2022, 6 pages.
Official Action for U.S. Appl. No. 16/347,147, dated Apr. 8, 2021, 8 pages. Restriction Requirement.
Official Action for U.S. Appl. No. 16/347,147, dated Jul. 2, 2021, 12 pages.
Official Action for U.S. Appl. No. 16/347,147, dated Nov. 12, 2021, 11 pages.
Official Action for U.S. Appl. No. 16/347,147, dated Jun. 2, 2022, 14 pages.
Official Action for U.S. Appl. No. 16/347,160, dated Dec. 28, 2020, 15 pages.
Official Action for U.S. Appl. No. 16/347,160, dated Nov. 29, 2021, 14 pages.
Official Action for U.S. Appl. No. 16/347,160, dated Jul. 7, 2022, 14 pages.
Official Action for U.S. Appl. No. 17/387,595, dated Nov. 10, 2021, 15 pages.
Official Action for U.S. Appl. No. 17/387,595, dated Mar. 28, 2022, 18 pages.
Official Action for U.S. Appl. No. 17/876,302, dated Oct. 25, 2022, 22 pages.
Official Action (with English translation) for China Patent Application No. 201980062844.X, dated Aug. 12, 2023, 30 pages.

* cited by examiner

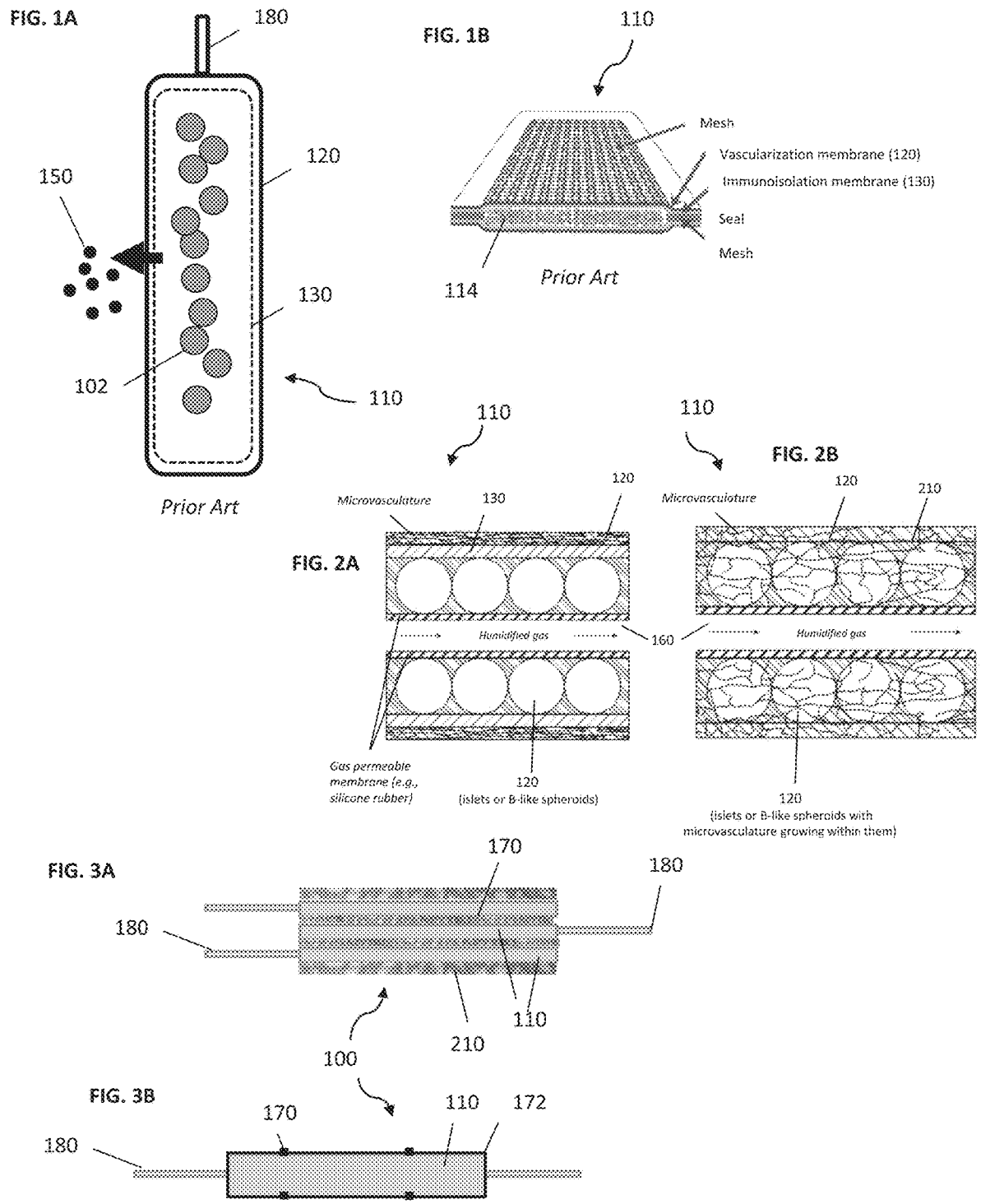

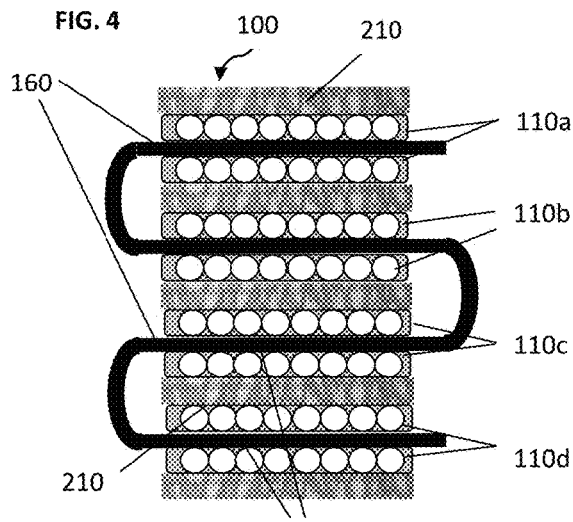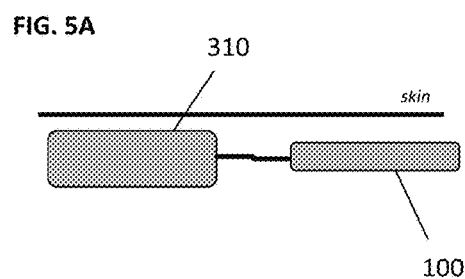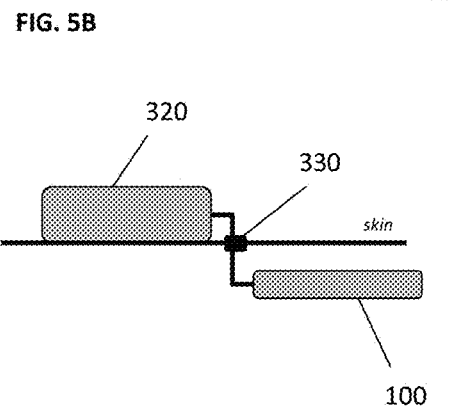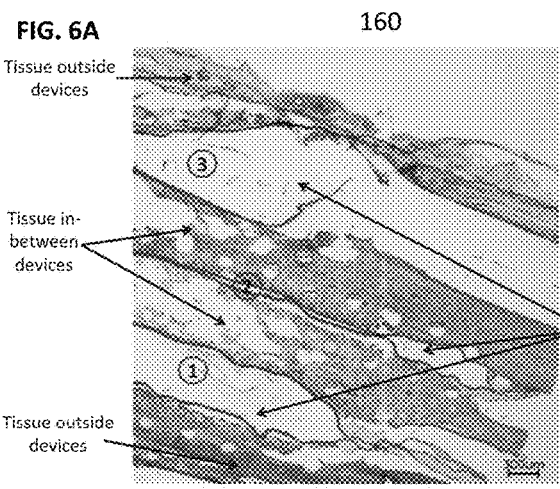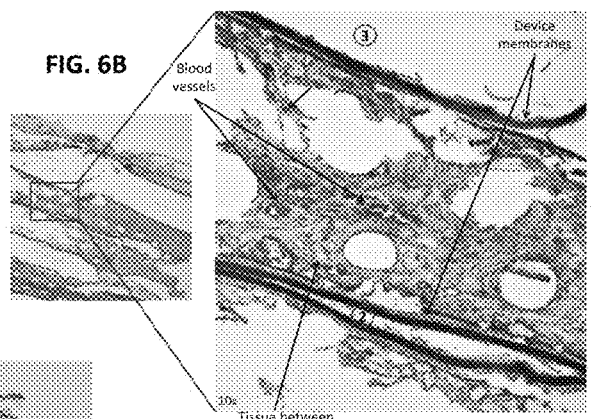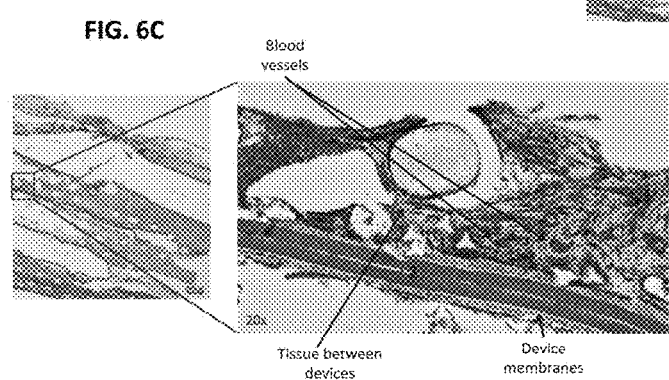

STACKED TISSUE ENCAPSULATION DEVICE SYSTEMS WITH OR WITHOUT OXYGEN DELIVERY

CROSS REFERENCE TO RELATED APPLICATIONS

This Continuation application claims priority to U.S. patent application Ser. No. 16/347,388, filed May 3, 2019, issued as U.S. Pat. No. 11,446,133, which is a national stage application under 35 U.S.C § 371 of and claims the benefit of PCT Application No. PCT/US2017/060034, filed Nov. 3, 2017, which claims the benefit of priority of U.S. Provisional Patent Application Ser. No. 62/417,017, filed Nov. 3, 2016, the entire disclosures of which are hereby incorporated by reference.

GOVERNMENT SUPPORT

This invention was made with government support under Grant No. DP3 DK106933, awarded by NIH. The government has certain rights in the invention.

FIELD OF THE INVENTION

The present invention relates to encapsulation devices for cells (such as but not limited to islet cells or stem cell derived beta cells or the like, e.g., for regulating blood glucose, or other cells or spheroids that can produce and release a therapeutic agent that is useful in the body), more particularly systems of encapsulation devices comprising two, three, or a plurality of encapsulation devices stacked together with the ability to form blood vessels around and in between them.

BACKGROUND OF THE INVENTION

Immunoisolation, or implantation of tissues in a membrane-enclosed device (encapsulation device), are approaches aimed at allowing maintenance of cells in an environment where they are segregated form the host tissues. A non-limiting example of an encapsulation device is shown in FIG. 1A and FIG. 1B.

It was surprisingly discovered that a system comprising stacked encapsulation devices (e.g., 4 devices) could be implanted and vascularization occurred in between the stacked devices. The system (stacked encapsulation devices) was easily explanted from animals without major bleeding, even with vasculature around and in between the stacked encapsulation devices.

The vascularization around and in between the system (stacked encapsulation devices) can help the delivery of oxygen and nutrients from the blood supply to the encapsulated cells while enabling the reduction in the required device footprint (the system with the stacked devices would take up less room than having each encapsulation device implanted separately next to each other) and may reduce or eliminate the need for exogenous oxygen delivery (typically, one of ordinary skill in the art would expect that if you are packing cells at a high density, exogenous oxygen delivery would be needed).

SUMMARY OF THE INVENTION

The present invention features systems comprising two or more encapsulation devices for cells that are stacked to create a thicker unit, e.g., two devices stacked, three devices stacked, four devices stacked, five devices stacked, six devices stacked, etc. Vascularization occurs within and around the system, which can help the delivery of oxygen and nutrients from the blood supply to the encapsulated cells while enabling the reduction in the required device footprint.

The connecting component does not cover the entire periphery so as to allow vasculature to grow between the devices.

The systems of the present invention may be used in conjunction with other therapies such as an artificial pancreas (e.g., a glucose sensor and an insulin infusion pump or a combination of the two and a control algorithm, etc.).

In some embodiments, cells are not present in the system or device upon implantation. In some embodiments, sensors may detect when oxygen is present in the encapsulation devices (e.g., vascularization has occurred), and cells may be subsequently injected into the device. In some embodiments, a user can determine how much oxygen is present in the system (or device) and determine how many cells to implant based on the oxygen level.

Implantation may be at any appropriate site, including but not limited to an arm location, a leg location, a torso location, etc.

The present invention features a system comprising at least a first encapsulation device stacked on a second encapsulation device and connected by a connecting component (e.g., a suture, etc.). The connecting component allows vasculature to grow between the two encapsulation devices (e.g., the two devices are not sealed to the point that they don't allow for cell penetration between them, e.g., as opposed to a full seal that doses off space between the devices so that vasculature cannot grow). The connecting component may space the devices apart. Wherein the first encapsulation device and the second encapsulation device each comprise a lumen for holding cells and a vascularization membrane (e.g., surrounding the cells). Vasculature may surround at least a portion of the system and is disposed in at least a portion of a space between the first encapsulation device and the second encapsulation device.

The first encapsulation device is separated from the second encapsulation device a particular distance (e.g., to allow vasculature growth). In some embodiments, the first encapsulation device further comprises an immunoisolation membrane in between the lumen and the vascularization membrane. In some embodiments, the second encapsulation device further comprises an immunoisolation membrane in between the lumen and the vascularization membrane. In some embodiments, the first encapsulation device and the second encapsulation device each comprise two lumens separated by a gas channel. In some embodiments, the gas channel of the first encapsulation device is fluidly connected to the gas channel of the second encapsulation device.

In some embodiments, the system further comprises cells disposed in the lumen of the first encapsulation device and the second encapsulation device. In some embodiments, the cells are for regulating blood glucose. In some embodiments, the cells for regulating blood glucose comprise islet cells or stem cell derived beta cells. In some embodiments, the cells comprise cells or spheroids that can produce and release a therapeutic agent.

In some embodiments, the lumen of the first encapsulation device or the lumen of the second encapsulation device comprises at least a small number of therapeutic cells that can survive and release pro-angiogenic factors that will enhance formation of blood vessels. In some embodiments, the system comprises a gel disposed between the first encapsulation device and the second encapsulation device.

In some embodiments, pro-angiogenic factors are embedded in the gel. In some embodiments, the pro-angiogenic factors can be slowly released to enhance vascularization.

In some embodiments, the system is operatively connected to an oxygen generator, e.g., an implantable oxygen generator, a wearable oxygen generator, etc.

In some embodiments, the system further comprises one or more additional encapsulation devices. For example, in some embodiments, the system comprises three encapsulation devices stacked together and connected by a connecting component. In some embodiments, the system comprises four encapsulation devices stacked together and connected by a connecting component. In some embodiments, the system comprises five encapsulation devices stacked together and connected by a connecting component. In some embodiments, the system comprises six encapsulation devices stacked together and connected by a connecting component. In some embodiments, the system comprises seven encapsulation devices stacked together and connected by a connecting component.

In some embodiments, the connecting component separates the encapsulation devices to allow vasculature to grow. In some embodiments, the system further comprises an oxygen sensor. In some embodiments, the oxygen sensor is disposed on an outer surface of the system. In some embodiments, the oxygen sensor is disposed in the system. In some embodiments, the oxygen sensor is disposed in a gas channel of the system. In some embodiments, the system further comprises a glucose sensor. In some embodiments, the system is implanted into a subject without cells in the lumens and cells are inserted into the lumens after implantation. In some embodiments, the encapsulation devices comprise loading ports for introducing cells to the lumens.

The present invention also features a system comprising at least a first encapsulation device stacked on a second encapsulation device and connected by a connecting component, and a third encapsulation device stacked on the second encapsulation device and connected by a connecting component, wherein the encapsulation devices each comprise a lumen for holding cells surrounded by a vascularization membrane. Or, the present invention also features a system comprising at least a first encapsulation device stacked on a second encapsulation device and connected by a connecting component, and a third encapsulation device stacked on the second encapsulation device and connected by a connecting component, and a fourth encapsulation device stacked on the third encapsulation device, wherein the encapsulation devices each comprise a lumen for holding cells surrounded by a vascularization membrane.

In some embodiments, vasculature surrounds at least a portion of the system and is disposed in at least a portion of a space between the first encapsulation device and the second encapsulation device and in at least a portion of a space between the second encapsulation device and the third encapsulation device and in at least a portion of a space between the third encapsulation device and the fourth encapsulation device. In some embodiments, vasculature surrounds at least a portion of the system and is disposed in at least a portion of a space between the first encapsulation device and the second encapsulation device and in at least a portion of the space between the second encapsulation device and the third encapsulation device.

In some embodiments, the gas channel of the first encapsulation device is fluidly connected to the gas channel of the second encapsulation device, which is fluidly connected to the gas channel of the third encapsulation device. In some embodiments, the gas channel of the first encapsulation device is fluidly connected to the gas channel of the second encapsulation device, which is fluidly connected to the gas channel of the third encapsulation device, which is fluidly connected to the gas channel of the fourth encapsulation device.

In some embodiments, the connecting component comprises a suture. In some embodiments, the encapsulation devices each further comprise an immunoisolation membrane in between the lumen and the vascularization membrane. In some embodiments, the encapsulation devices each comprise two lumens separated by a gas channel.

In some embodiments, the system further comprises cells disposed in the lumen of each encapsulation device. In some embodiments, the cells are for regulating blood glucose. In some embodiments, the cells for regulating blood glucose comprise islet cells or stem cell derived beta cells. In some embodiments, the cells comprise cells or spheroids that can produce and release a therapeutic agent. In some embodiments, the lumens of the encapsulation devices comprise at least a small number of therapeutic cells that can survive and release pro-angiogenic factors that will enhance formation of blood vessels.

In some embodiments, the system comprises a gel disposed between the encapsulation devices. In some embodiments, pro-angiogenic factors are embedded in the gel. In some embodiments, the pro-angiogenic factors can be slowly released to enhance vascularization.

In some embodiments, the system is operatively connected to an oxygen generator. In some embodiments, the oxygen generator is an implantable oxygen generator. In some embodiments, the oxygen generator is a wearable oxygen generator.

In some embodiments, the connecting component separates the encapsulation devices to allow vasculature to grow.

In some embodiments, the system comprises an oxygen sensor. In some embodiments, the system comprises a glucose sensor. In some embodiments, the system is implanted into a subject without cells in the lumens and cells are inserted into the lumens after implantation.

The disclosures of the following U.S. Patents are incorporated in their entirety by reference herein: U.S. Pat. No. 5,713,888; U.S. Pat. App. No. 2003/0087427.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which:

FIG. 1A shows an example of a single-chamber encapsulation device for holding cells or tissues. The device comprises a port to access the lumen for loading the cells or tissue.

FIG. 1B shows a cross-sectional view of the device of FIG. 1A. The cells are encapsulated in a two-layer membrane envelope formed using a mesh insert. The device comprises a vascularization membrane and an immunoisolation membrane. The present invention is not limited to devices that utilize an immunoisolation membrane: in some embodiments, the device only comprises the vascularization membrane.

FIG. 2A shows a detailed view of an encapsulation device with an immunoisolation membrane. The device has two lumens or chambers with cells separated by a gas chamber.

FIG. 2B shows a detailed view of an encapsulation device without the immunoisolation membrane. The device has two lumens or chambers with cells separated by a gas chamber.

FIG. 3A shows a side view of a schematic of a system of the present invention comprising three encapsulation devices.

FIG. 3B shows a top view of the system of FIG. 3A.

FIG. 4 shows a schematic view of a system comprising four encapsulation devices stacked atop each other, each device with two lumens separated by a gas channel.

FIG. 5A shows a schematic view of a system connected to an implantable oxygen generator.

FIG. 5B shows a schematic view of a system connected to a wearable oxygen generator.

FIG. 6A shows an H&E stain of the system of Example 1 (three 40 μL devices stacked).

FIG. 6B shows an H&E stain of the system of Example 1 (three 40 μL devices stacked).

FIG. 6C shows an H&E stain of the system of Example 1 (three 40 μL devices stacked).

DETAILED DESCRIPTION OF THE INVENTION

Encapsulation Devices

Figure 7A:
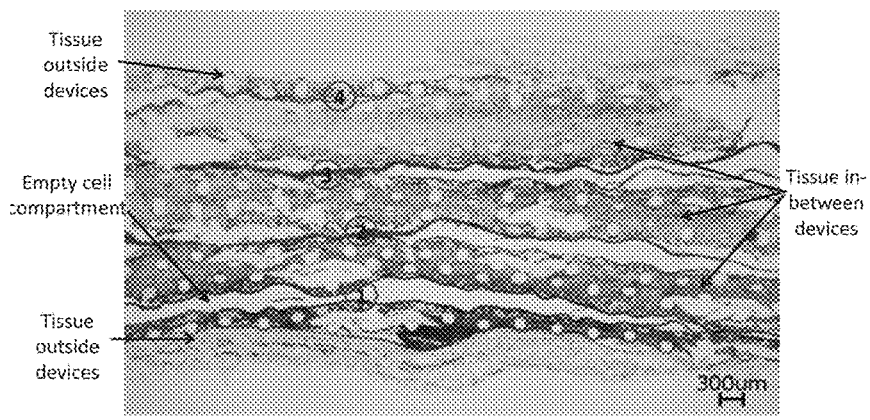
FIG. 7A shows an H&E stain of the 4.5 μL chamber system of Example 2.

Encapsulation devices are devices for holding cells or tissues. The encapsulation device (110) shown in FIG. 1A is a single-chamber encapsulation device. The device (100) comprises an inner lumen for holding the cells (102) or tissue and at least one membrane, e.g., a vascularization membrane (120), which is impermeable to cells. In some embodiments, the device (100) further comprises an immunoisolation membrane (130). Non-cell factors or molecules (150) can escape the cell impermeable membrane. The device (110) also comprises a port (180) to access the lumen for loading the cells or tissue. FIG. 1B shows a cross-sectional view of an encapsulation device. The cells are encapsulated in a lumen (114) by a two-layer membrane envelope, a vascularization membrane (120) and an immunoisolation membrane (130). The device (110) also has structural support, e.g., mesh, seals, etc.

In some embodiments, the encapsulation devices (110) comprise a vascularization membrane (120) and immunoisolation membrane (130). In some embodiments, the encapsulation devices (110) comprise just the vascularization membrane (120). This allows blood vessels to grow within the transplanted tissue.

In the examples shown in FIG. 1A and FIG. 1B, the cells therein are about 5-15 μm in diameter. The outer membrane, the vascularization membrane (120), has a pore size from 5-10 μm. The vascularization membrane (120) is about 15 μm thick. The immunoisolation membrane (130) has a pore size of about 0.4 μm. The immunoisolation membrane (130) is about 30 μm thick. In some embodiments, the membranes (120, 130) are constructed from materials such as polytetraflouroethylene (PTFE) or other similar material. The present invention is not limited to the aforementioned pore sizes and thicknesses of the membranes used therein. The present invention is not limited to the aforementioned materials.

The encapsulation devices (110) may be constructed in various shapes and sizes and with various lumen volumes. For example, in some embodiments, the lumen has a volume of about 4.5 μl. In some embodiments, the lumen has a volume of 20 μl. In some embodiments, the lumen has a volume of 40 μl. In some embodiments, the device (110) is from 4 to 5 cm in length. In some embodiments, the device (110) is from 2 to 5 cm in length, e.g., 3 cm. In some embodiments, the device (110) is from 5 to 10 cm in length. The present invention is not limited to the aforementioned dimensions and lumen volumes. For example, in some embodiments, the lumen has a volume of about 100 μl. In some embodiments, the lumen has a volume of about 200 μl. In some embodiments, the lumen has a volume from 2 to 50 μl. In some embodiments, the lumen has a volume from 10 to 100 μl. In some embodiments, the lumen has a volume from 40 to 200 μl. In some embodiments, the lumen has a volume from 100 to 300 μl. In some embodiments, the lumen has a volume from 200 to 500 μl.

In some embodiments, within the encapsulation devices (110), there may be layers of cells or tissue, e.g., multiple lumens within the device (110). For example, an encapsulation device (110) may comprise two chambers or lumens. In some embodiments, the device comprises more than two chambers or lumens, e.g., 3 chambers or lumens, 4 chambers or lumens, 5 chambers or lumens, etc. FIG. 2A and FIG. 2B show examples an encapsulation with two lumens (two chambers) that are separated by a gas channel (160). FIG. 2A and FIG. 2B also show vascularizing membrane and microvasculature. The blood vessels embed into the vascularizing membrane.

In some embodiments, the chamber or lumen comprises a single layer of cells. In some embodiments, the chamber or lumen comprises two layers of cells. In some embodiments, the chamber comprises three or more layers of cells. In some embodiments, islet spheroids (about 150 um in size) are used (shown in FIG. 2A, FIG. 2B). In some embodiments, a dual layer of the islet spheroids is used (lumen thickness would be about 300 um in the chamber or in each chamber). In some embodiments, a third layer is supported depending on the metabolic activity and other characteristics of the spheroids/cells used. Note spheroids may not be touching each other in some configurations and the space between them may be 1 or 2 spheroids apart (e.g., 150 um, 300 um), or more or less.

Systems with Stacked Encapsulation Devices

The present invention features a system (100) comprising two or more stacked encapsulation devices (110), e.g., a first encapsulation device and a second encapsulation device. The cells used in the various encapsulation devices of the system (100) may include but are not limited to islet cells or stem cell derived beta cells or the like, e.g., for regulating blood glucose, or other cells or spheroids that can produce and release a therapeutic agent that is useful in the body. The cells in the different encapsulation devices (110) may be the same, similar, or various different combinations of cells may be included within the encapsulation devices or throughout the stacked devices. For example, in a system (100) with two encapsulation devices (110), the cells in the first encapsulation device may be the same as the cells in the second encapsulation device. Or, in some embodiments, the cells in the first encapsulation device maybe the different from the cells in the second encapsulation device.

In some embodiments, the system (100) comprises two encapsulation devices (110). In some embodiments, the system comprises three encapsulation devices. In some embodiments, the system comprises four encapsulation devices. In some embodiments, the system comprises five encapsulation devices. In some embodiments, the system comprises six encapsulation devices. In some embodiments, the system comprises more than six encapsulation devices, e.g., seven devices, eight devices, nine devices, ten devices, more than ten devices, etc. The system shown in FIG. 3A and FIG. 3B comprises three encapsulation devices (110).

The stacked devices (110) of the system (100) may be connected together, e.g., to prevent sliding. In some embodiments, the devices (110) are sutured together (see FIG. 3A). In some embodiments, the devices (110) are connected via other means (e.g., welding but with unwelded spaces between them so as to avoid blocking blood vessels). FIG. 3A shows sutures (170) or spacers linking the different devices (110). FIG. 3A also shows the vasculature (210) around and within the system (100). Note the vasculature may encompass the entire system (100), which is not shown in FIG. 3A or FIG. 3B. A seal (172) is shown surrounding the device in FIG. 3B.

The connecting components space the encapsulation devices apart to allow vasculature to grow between them.

The stacked devices (110) of the system (100) are configured (e.g., spaced a distance apart) to allow for vascularization between the individual devices.

As previously discussed, the encapsulation devices (110) may be constructed in a variety of sizes and with a variety of different lumen volumes. In some embodiments, the devices (110) in the system (100) are uniform in length and/or lumen volume. In some embodiments, one or more of the devices (110) in the system (100) has a different length and/or lumen volume. For example, a first device (110) may be about 4.5 cm in length and a second device may be about 2 cm in length.

In some embodiments, the systems or devices of the present invention feature a sealant and/or a scaffold disposed between the individual encapsulation devices. Scaffold or sealant materials may include but are not limited to a gel, e.g., fibrin (e.g., fibrin sealant). The scaffold or sealant allows for vascularization to occur.

Incorporation of Oxygen Delivery

Without wishing to limit the present invention to any theory or mechanism, one of ordinary skill in the art may believe that adding oxygen to the system may inhibit vessel growth, e.g., the opposite of what occurs in hypoxic situations that stimulate vessel growth. However, the system of the present invention may be used with oxygen (or air) delivery. In some embodiments, an oxygen delivery system is integrated into the system, e.g., integrated within the individual stacked encapsulation devices. The amount of oxygen supplied to the systems (if applicable), may vary, e.g., low oxygen may be supplied, atmospheric oxygen levels may be supplied, higher oxygen levels may be supplied, etc.

The present invention is not limited to systems that feature oxygen delivery. In some embodiments, exogenous oxygen is not incorporated into the system.

In some embodiments, the system (100) of the present invention comprises a channel, such as a gas channel (160) for delivery of the gas or other fluids (e.g., with nutrients) to the cells in an encapsulation device (e.g., to multiple lumens inside a single encapsulation device). As shown in FIG. 4, a gas channel may fluidly connect two or more individual encapsulation devices. The gas channel (160) in FIG. 4 is disposed in between two lumens of a first encapsulation device and extends out of the device and into a second encapsulation device in between its two lumens.

FIG. 4 shows a system (100) comprising a first encapsulation device (110a) with two lumens separated by a gas chamber (160) stacked atop a second encapsulation device (110b) with two lumens separated by a gas chamber (160) stacked atop a third encapsulation device (110c) with two lumens separated by a gas chamber (160) stacked atop a fourth encapsulation device (110d) with two lumens separated by a gas chamber (160). The gas chambers (160) are fluidly connected such that gas flows through the first device (110a) to the second device (110b) to the third device (110c) to the fourth device (110d) and out of the fourth device (110d). Vascularization (210) is present around and between the four devices (110).

In some embodiments, the devices of the systems of the present invention are temporarily oxygenated. For example, in some embodiments, oxygen is temporarily delivered initially (e.g., initially upon implantation) until the system is adequately vascularized. In some embodiments, oxygen may be temporarily delivered and/or oxygen levels may be variable. For example, in some embodiments, a cell type is used that benefits from a high oxygen level. In some embodiments, a cell type is used that benefits from a low oxygen level (e.g., 15% or lower). In some embodiments, an oxygen level of about 21% oxygen (e.g., 20-22%) is used, e.g., air may be used. In some embodiments, an oxygen level from 15-22% is used. In some embodiments, an oxygen level from 10-15% is used. In some embodiments, an oxygen level from 5-10% is used. In some embodiments, an oxygen level from 0-5% is used. In some embodiments, a particular oxygen level is used initially and then the oxygen level is increased or decreased at a later time. In some embodiments, oxygen is turned on and then off. In some embodiments, oxygen is turned off and then on. In some embodiments, oxygen is turned on and off in a cycle for a period of time or indefinitely. In some embodiments, oxygen level is tailored to the application to help modulate the local immune system by providing temporary oxygen. In some embodiments, oxygen levels are tailed to when vascularization occurs. In some embodiments, immature cells are transplanted, and low oxygen levels may be used initially; as the cells mature (e.g., after a particular time, e.g., 4-6 weeks), higher oxygen levels may be provided.

Referring to FIG. 5A and FIG. 5B, oxygen may be delivered to the systems via several different mechanisms. For example, in FIG. 5A, the system (100) is operatively and fluidly connected to an implantable oxygen generator (310). Tubing delivers gas to the gas channel (160) of the system (100). Implantable oxygen generators are well known to one of ordinary skill in the art. For example, the implantable oxygen generator may feature an electrochemical oxygen generation mechanism (e.g., using electricity to break down water to oxygen hydrogen), a chemical mechanism, or other mechanism. In FIG. 5B, the system (100) is operatively and fluidly connected to a wearable oxygen generator (320) or pump via tubing. A special device (330) may be implanted into the skin to help prevent infection.

In some embodiments, the oxygen is delivered via a carrier media like hemoglobin or fluorinated microbubbles. The present invention is not limited to the aforementioned systems or materials.

In some embodiments, there is a contiguous gas supply through each of the devices (110).

Sensors

In some embodiments, the system features one or more sensors disposed on or in one or more places of the system (100). For example, in some embodiments, a sensor is disposed in the gas channel (160). In some embodiments, a sensor is disposed in a lumen of a device (110). In some embodiments, a sensor is disposed on the outer surface of a device (110). Sensors may include but are not limited to oxygen sensors, glucose sensors, lactate sensors, or other appropriate sensors. In some embodiments, the system comprises a means (e.g., a sensor) for determining when the cells are dead (e.g., via oxygen sensors, etc.).

Without wishing to limit the present invention to any theory or mechanism, cells are likely dead if there is generally no difference in oxygen levels inside and outside the device. Typically there is a difference (a gradient) in oxygen levels between the inside and outside of the device because oxygen is being consumed by live cells. Thus, no difference would be indicative of no oxygen consumption, thus the cells are likely dead. A bigger difference (gradient) in oxygen levels between the inside and outside of the device would indicate there are more viable cells. A user may determine how many cells are dying by determining the change in oxygen gradient.

As previously discussed, the systems or devices may be implanted at any appropriate site, including but not limited to an arm location, a leg location, a torso location, etc.

Example 1

Figure 7B:
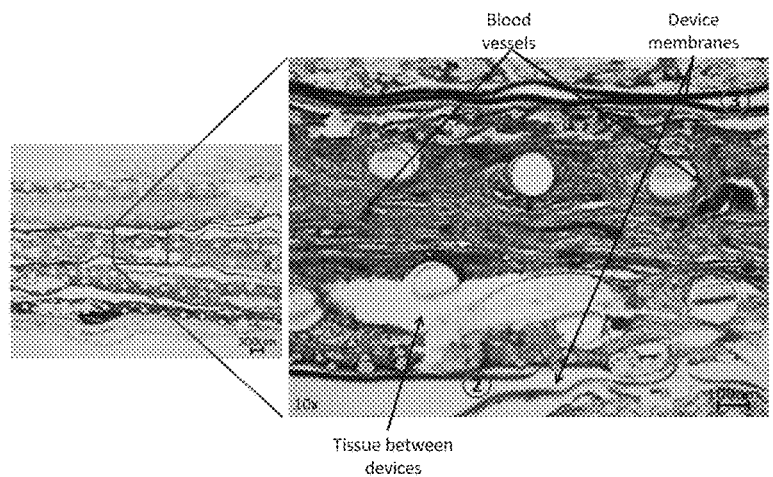
FIG. 7B shows an H&E stain of the 4.5 μL chamber system of Example 2.
Figure 7C:
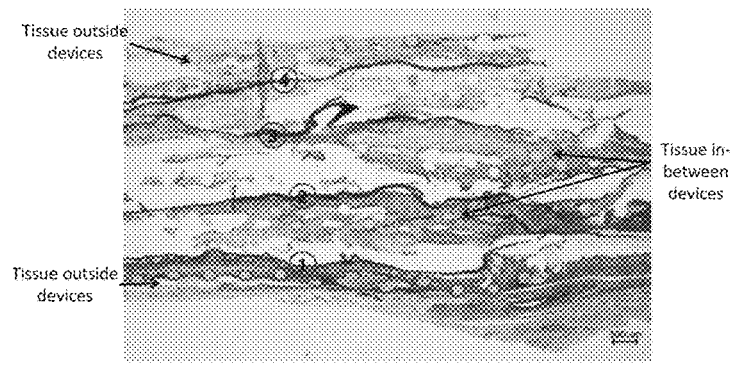
FIG. 7C shows an H&E stain of the 20 μL chamber system of Example 2.
Figure 7D:
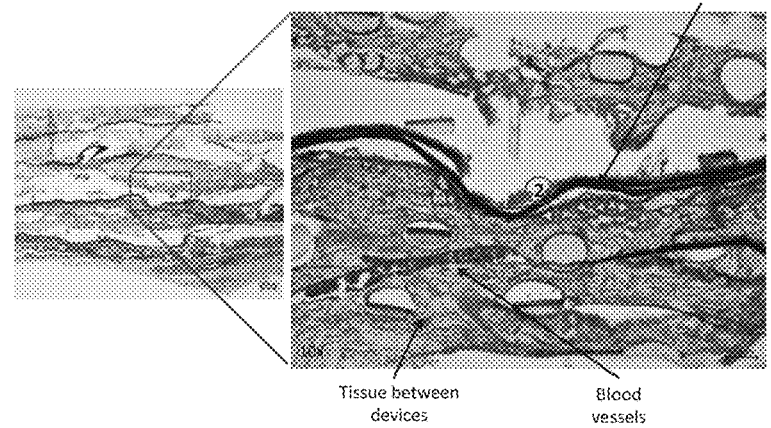
FIG. 7D shows an H&E stain of the 20 μL chamber system of Example 2.

Three 40 μL 1-chamber encapsulation devices were stitched together at four spots (top, bottom, and sides) using 3-0 silk suture. Devices were placed on top of each other with the loading ports facing opposite directions (see FIG. 3A). A system with the three empty 40 μl-chamber encapsulation devices was implanted subcutaneously into one althymic nude rat. The system was implanted for 24 days. On day 24, the system was explanted and processed for histology. The system was paraffin embedded, sectioned, and stained with H and E (Hematoxylin, nuclei in purple, and Eosin, cytoplasm in pink). Images were collected using Keyence BZ-X700 Fluorescence microscope. Resulting images are shown in FIG. 6, FIG. 7, and FIG. 8.

Example 2

Four 4.5 μL 1-chamber encapsulation devices and four 20 μL 1-chamber were stitched together at four spots (top, bottom, and sides) using 3-0 silk suture. Devices were placed on top of each other with the loading ports facing opposite directions (see FIG. 3A for example). The system with four empty 4.5 μL 1-chamber encapsulation devices was implanted subcutaneously into one althymic nude rat and the system with four 20 μL 1-chamber encapsulation devices was implanted subcutaneous into another althymic nude rat. The 4.5 μL system was transplanted for 45 days then explanted. The 20 μL system was transplanted for 60 days and then explanted. Both systems were processed for histology. The systems were paraffin embedded, sectioned, and stained with H and E (Hematoxylin, nuclei in purple, and Eosin, cytoplasm in pink). Images were collected using Keyence BZ-X700 Fluorescence microscope. Resulting images are shown in FIG. 9, FIG. 10, FIG. 11, and FIG. 12.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An implantable encapsulation device comprising:
   a first lumen and a second lumen;
   a channel operable to deliver fluid to at least one of the first lumen and the second lumen, and wherein at least one of the first lumen and the second lumen at least partially encapsulates the channel, and wherein the channel comprises a continuous channel that extends along at least a portion of the first lumen and the second lumen; and
   a vascularization membrane at least partially encapsulating at least one of the first lumen and the second lumen and wherein the vascularization membrane is operable to permit the ingrowth of vascularization;
   wherein the first lumen is stacked atop the second lumen with space provided between the first and second lumens;
   wherein the first lumen and the second lumen are stacked and separated by the channel; and
   wherein first and second connecting components are provided to secure the relative position of the first lumen and the second lumen and prevent sliding of the lumens relative to one another.

2. The system of claim 1, wherein the first lumen is provided within a first encapsulation
   device and the second lumen is provided within a second encapsulation device.

3. The system of claim 2, wherein the device comprises an immunoisolation membrane
   comprising pores that are smaller than pores of the vascularization membrane.

4. The system of claim 1, further comprising cells provided in at least one of the first lumen
   and the second lumen and wherein the cells are operable to produce and release a therapeutic
   agent.

5. The system of claim 1, wherein the system further comprises an oxygen generator.

6. The system of claim 1, wherein the system comprises at least one sensor.

7. An implantable encapsulation device comprising:
- a first lumen and a second lumen;
- a channel operable to deliver fluid to at least one of the first lumen and the second lumen, and wherein at least one of the first lumen and the second lumen at least partially encapsulates the channel, and wherein the channel comprises a continuous channel that extends along at least a portion of the first lumen and the second lumen; and
- a vascularization membrane operable to permit vascularization;
- wherein the first lumen is stacked atop the second lumen;
- wherein the first lumen and the second lumen are stacked and separated by the channel; and
- wherein connecting components are provided to secure the relative positions of the first lumen and the second lumen and prevent sliding of the lumens relative to one another.

8. The system of claim 7, wherein the first lumen is provided within a first encapsulation device and the second lumen is provided within a second encapsulation device.

9. The system of claim 8, wherein the device comprises an immunoisolation membrane comprising pores that are smaller than pores of the vascularization membrane.

10. The system of claim 7, further comprising cells provided in at least one of the first lumen and the second lumen and wherein the cells are operable to produce and release a therapeutic agent.

11. The system of claim 7, wherein the system further comprises an oxygen generator.

12. The system of claim 7, wherein the system comprises at least one sensor.

13. An implantable encapsulation device comprising:
- a plurality of stacked lumens secured by two or more connecting components to prevent sliding and secure the relative positions of the lumens;
- a channel operable to deliver fluid to at least one of the plurality of lumens, and wherein at least one lumen at least partially encapsulates the channel, and wherein the channel comprises a continuous channel that extends along at least a portion of the plurality of lumens; and
- a vascularization membrane operable to permit vascularization;
- wherein space is provided between the lumens;
- wherein the plurality of lumens is separated by the channel; and
- wherein the space is operable to at least one of permit vascularization and receive a gas delivery device.

14. The system of claim 13, wherein the device comprises at least three lumens.

15. The system of claim 13, wherein the device comprises an immunoisolation membrane comprising pores that are smaller than pores of the vascularization membrane.

16. The system of claim 13, further comprising cells provided in at least one of the lumens and wherein the cells are operable to produce and release a therapeutic agent.

17. The system of claim 13, wherein the system further comprises an oxygen generator.

\* \* \* \* \*